(12) United States Patent
Urazoe et al.

(10) Patent No.: US 7,390,927 B2
(45) Date of Patent: Jun. 24, 2008

(54) PROCESS FOR PREPARING 3-AMINOPHENYLACETYLENES

(75) Inventors: Daisuke Urazoe, Kanagawa (JP); Hideto Mori, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 111 days.

(21) Appl. No.: 11/392,717

(22) Filed: Mar. 30, 2006

(65) Prior Publication Data

US 2006/0224016 A1  Oct. 5, 2006

(30) Foreign Application Priority Data

Mar. 31, 2005  (JP) ............................. 2005-105039

(51) Int. Cl.
  *C07C 209/68* (2006.01)
(52) U.S. Cl. ..................... 564/305; 564/409; 564/437; 564/443
(58) Field of Classification Search ............... 564/305, 564/409, 437, 443
See application file for complete search history.

(56) References Cited

U.S. PATENT DOCUMENTS 4,216,341 A * 8/1980 Onopchenko et al. ....... 564/418
5,902,902 A   5/1999 Cabri et al.

OTHER PUBLICATIONS

Tsutomu Takeichi et al., Macromolecules vol. 19, No. 8, Aug. 1986, pp. 2093 to 2102.
Anatoli Onopchenko et al.; J. Org. Chem., vol. 44, No. 8, pp. 1233-1236, 1979.
Anatoli Onopchenko et al.; J. Org. Chem., vol. 44, No. 21, pp. 3671-3674, 1979.

* cited by examiner

*Primary Examiner*—Peter O'Sullivan
(74) *Attorney, Agent, or Firm*—Birch, Stewart, Kolasch & Birch, LLP

(57) ABSTRACT

A process for preparing a 3-aminophenylacetylene compound of formula (5), including: a) reacting a 3-haloaniline compound of formula (1) with an acetylene compound of formula (2) in the presence of a palladium compound, a copper compound, and an amine compound of formula (3) to form an aniline compound of formula (4); b) precipitating the aniline compound of formula (4) in the form of a crystal, and isolating it by solid/liquid separation; and c) reacting the aniline compound of formula (4) with a base to obtain 3-aminophenylacetylene.

18 Claims, 1 Drawing Sheet

PROCESS FOR PREPARING 3-AMINOPHENYLACETYLENES

CROSS-REFERENCE TO RELATED APPLICATION

This application claims priority under 35 USC 119 from Japanese Patent Application No. 2005-105039, the disclosure of which is incorporated by reference herein.

BACKGROUND OF THE INVENTION

1. Field of the Invention

The present invention relates to a process for preparing 3-aminophenylacetylenes useful as synthetic raw materials for pharmaceutical and agricultural chemicals, thermosetting resins, nonlinear optical materials, and the like.

2. Description of the Related Art 3-aminophenylacetylenes are interesting compounds having an amino group capable of forming polyimide, polyimine, or the like, and an acetylene group having polymerizability both present in the same molecule, and have received attention as the objects of study in various fields. They are useful as, for example, synthetic intermediates for thermosetting resins (see, for example, U.S. Pat. Nos. 4,485,231, 4,442,278, and 5,138,028, and JP-A-4-275259), nonlinear optical materials (see, for example, JP-A-1-233263, and JP-A-63-68549), pharmaceutical and agricultural chemicals (see, for example, U.S. Pat. No. 5,360,802, JP-A-57-118568, and JP-A-59-164160), and the like.

As described above, 3-aminophenylacetylenes has been used for various purposes in many fields and a variety of processes for preparing the same have been known. The processes known heretofore can be broadly divided into two types: (1) a process involving a reduction of only the nitro group present in a precursor having both an acetylene group and a nitro group; and (2) a process not involving a step of forming a nitro intermediate.

As the processes of type (1), there are known a process in which 3-nitrophenylacetylene is condensed with an acetone and the resultant condensation derivatives is reduced using a Ru catalyst (see, for example, *J. Org. Chem.*, vol. 44, p. 1233 (1979)), using cobalt polysulfide (CoSx) or ruthenium (IV) sulfide (see, for example, *J. Org. Chem.*, vol. 44, p. 3671, (1979)), or using an iron or an iron salt (see, for example, JP-A-10-36325).

As the processes via route (2), there are known a process in which trialkylstannyl acetylene which is an organotin compound and 3-iodoaniline are subjected to coupling in the presence of a palladium catalyst (see, for example, *Macromolecules*, vol. 19, p. 2093 (1986)); and a process comprising reacting a 3-haloaniline with a protected acetylene compound in the presence of a strong base, a palladium compound, and a copper compound (see, for example, U.S. Pat. No. 5,902,902).

Further, in the process according to U.S. Pat. No. 5,902,902, the use of diazabicyclooctane, diazabicycloundecane, and 1,1,3,3-tetramethylguanidine as the preferred strong bases in the reaction between 3-haloaniline and an acetylene compound is exemplified.

On the other hand, in recent years, the burden of chemical preparing processes on the environment has become a problem. This has resulted in demands for a clean chemical reaction leaving less waste, and using a minimum of harmful solvents, reaction agents, or the like (see, for example, *Kagaku Frontier* 4 (*Green Chemistry*), Kagaku Doujinn, translated by GSC Network, Nov. 30, 2001).

In the preparing process through route (1), it is important to reduce only a nitro group in the system where an acetylene group and a nitro group are both present in a molecule. In actuality, however, it is difficult to implement perfect selectivity to the reduction of nitro group only. Further, the process requires the preparation of a special catalyst such as cobalt polysulfide (CoSx), and the removal of the iron compound used as a reducing agent which after-treatment thereof is complicated. These and other aspects have caused not only an increase in cost but have also led to complication of operations including waste disposal.

On the other hand, the process not involving a step of forming a nitro intermediate of route (2) avoids the problem regarding reduction. However, in the process disclosed in the literature *Macromolecules*, vol. 19, p. 2093 (1986), a toxic organotin compound is used, which is not fit for preparation on an industrial scale from the viewpoint of the environment.

Also, the strong bases such as diazabicyclooctane, diazabicycloundecane, and 1,1,3,3-tetramethylguanidine in U.S. Pat. No. 5,902,902 are relatively expensive. In addition, the process of U.S. Pat. No. 5,902,902 is a process in which a reaction product is extracted with methylene chloride, followed by purification by silica gel column chromatography. This process is thus not fit for preparation on an industrial scale because of the complicated operations, and has also presented a problem from the viewpoint of the waste material.

Thus, conventional processes can not be said by any means to be an advantageous process in view of ease of operation, safety, preparing cost, throughput per reaction, separation and purification of the target substance, consideration of the environment, and the like.

SUMMARY OF THE INVENTION

The present invention has been made in consideration of the above problems of the conventional processes. That is, the present invention provides a process for preparing 3-aminophenylacetylenes, which can minimize waste materials and can be carried out economically on an industrial scale without using compounds and solvents which are undesirable for the environment.

A first aspect of the invention is a process for preparing a 3-aminophenylacetylene compound represented by formula (5) comprising:

a) reacting a 3-haloaniline compound represented by formula (1) with an acetylene compound represented by formula (2) in the presence of a palladium compound, a copper compound, and an amine compound represented by formula (3), to produce an aniline compound represented by formula (4);

b) precipitating the resultant aniline compound represented by formula (4) in the form of a crystal, and isolating it by solid/liquid separation; and c) reacting the aniline compound represented by formula (4) obtained in the above b) with a base to obtain 3-aminophenylacetylene represented by formula (5):

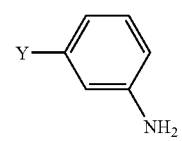

formula (1)

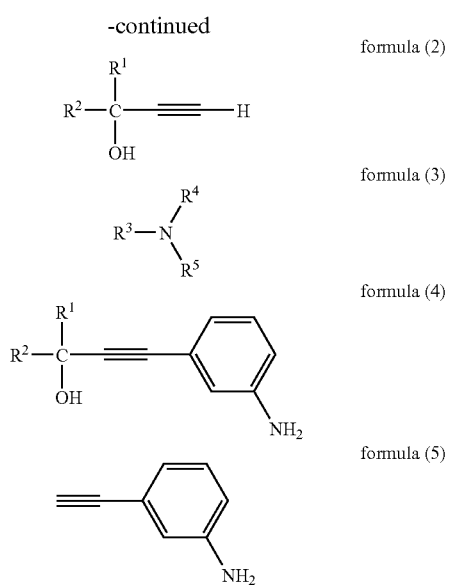

wherein formulae (1) to (4), Y represents a halogen atom; $R^1$ and $R^2$ each independently represent a hydrogen atom, a substituted or unsubstituted alkyl group having 1 to 6 carbon atoms, a substituted or unsubstituted cycloalkyl group having 3 to 6 carbon atoms or a substituted or unsubstituted aryl group having 6 to 12 carbon atoms, or, $R^1$ and $R^2$ may combine with each other to form a ring; $R^3$ represents a hydrogen atom, a substituted or unsubstituted alkyl group having 1 to 6 carbon atoms or a substituted or unsubstituted cycloalkyl group having 3 to 6 carbon atoms; $R^4$ and $R^5$ each independently represent a substituted or unsubstituted alkyl group having 1 to 6 carbon atoms, a substituted or unsubstituted cycloalkyl group having 3 to 6 carbon atoms or a substituted or unsubstituted aryl group having 6 to 12 carbon atoms, or $R^4$ and $R^5$ may combine with each other to form a ring.

A second aspect of the invention is the process according to the first aspect, wherein the amine compound represented by formula (3) is selected from the group consisting of diethylamine, diisopropylamine, piperidine, pyrrolidine, N-methylmorpholine, N-methylpiperidine, triethylamine, tri-n-propylamine, tri-n-butylamine, diisopropylethylamine, N,N-dimethylaniline, and N,N-diethylaniline.

A third aspect of the invention is the process according to the first aspect, wherein the amount of the amine compound represented by formula (3) is within the range of 1.0 to 20.0 equivalents based on the amount of the 3-haloaniline compound represented by formula (1).

A fourth aspect of the invention is the process according to the first aspect, wherein the palladium compound is a palladium compound represented by $PdX_2$ coordinated to a phosphine compound, wherein X represents a chloride ion, a bromide ion, an iodide ion, an acetic acid ion, acetyl acetonate, or dibenzyl acetonate.

A fifth aspect of the invention is the process according to the fourth aspect, wherein the palladium compound is a palladium compound represented by formula (P1), (P2), or (P3):

$L_2PdX_2$     Formula (P1):

$(L-L)PdX_2$     Formula (P2):

$PdL_4$     Formula (P3):

wherein in formulae (P1) and (P3), L represents a monodentate phosphine compound represented by $P(R^6)(R^7)(R^8)$ in which $R^6$ to $R^8$ each independently represent a hydrocarbon group such as an aryl group or an alkyl group, and at least two of $R^6$ to $R^8$ may combine with each other to form a ring; and in formulae (P1) and (P2), X represents a chloride ion, a bromide ion, an iodide ion, an acetic acid ion, acetyl acetonate, or dibenzyl acetonate, and in the formula (P2), (L–L) represents a bidentate phosphine compound or a bidentate nitrogen compound.

A sixth aspect of the invention is the process according to the fifth aspect, wherein the amount of each palladium compound represented by formulae (P1), (P2) or (P3) is within the range of $1.0 \times 10^{-8}$ to $5.0 \times 10^{-2}$ equivalent based on the amount of a 3-haloaniline compound represented by formula (1).

A seventh aspect of the invention is the process according to the fourth aspect, wherein the palladium compound represented by $PdX_2$ and a phosphine compound coordinating thereto are added in the reaction system to effect the reaction.

An eighth aspect of the invention is the process according to the seventh aspect, wherein the amount of the phosphine compound is within the range of 1.0 to 100 equivalents based on the amount of the palladium compound represented by $PdX_2$.

A ninth aspect of the invention is the process according to the first aspect, wherein the copper compound is one or more monovalent copper compounds selected from the group consisting of copper (I) chloride, copper (I) bromide, copper (I) iodide, copper (I) acetate, and copper (I) cyanide.

A tenth aspect of the invention is the process according to the first aspect, wherein a quaternary ammonium salt is further used in the step a).

An eleventh aspect of the invention is the process according to the tenth aspect, wherein the quaternary ammonium salt is selected from the group consisting of tetraethylammonium bromide, tetraethylammonium iodide, benzyl tributylammonium chloride, benzyl tributylammonium iodide, benzyl triethylammonium bromide, benzyl triethylammonium chloride, benzyl trimethylammonium bromide, and benzyl trimethylammonium chloride.

A twelfth aspect of the invention is the process according to the tenth aspect, wherein the amount of the quaternary ammonium salt is within the range of $1.01 \times 10^{-2}$ to $5.0 \times 10^{-1}$ equivalent based on the amount of a 3-haloaniline compound represented by formula (1).

A thirteenth aspect of the invention is the process according to the first aspect, wherein the reaction temperature of the step a) is within the range of 20 to 200° C.

A fourteenth aspect of the invention is the process according to the first aspect, wherein the solvent system for crystallizing the aniline compound represented by formula (4) comprises an organic solvent selected from the group consisting of alcohol type solvents, ether type solvents, ester type solvents, acetonitrile, and propionitrile used alone, or a mixture of one or more of these organic solvents with a nonpolar organic solvent selected from the group consisting of aliphatic hydrocarbon solvents and aromatic hydrocarbon solvents.

A fifteenth aspect of the invention is the process according to the first aspect, wherein the temperature for precipitating the crystal is 50° C. or less.

A sixteenth aspect of the invention is the process according to the first aspect, wherein the base in the step c) is selected from the group consisting of a hydroxide, a carbonate, or an alkoxide of an alkali metal, and a hydroxide, a carbonate, or an alkoxide of an alkaline-earth metal.

A seventeenth aspect of the invention is the process according to the first aspect, wherein the amount of the base is within the range of 0.05 to 3.0 equivalents based on the amount of the aniline compound represented by formula (4).

An eighteenth aspect of the invention is the process according to the first aspect, wherein the reaction temperature in the step c) is within the range of 60 to 200° C.

DESCRIPTION OF THE PRESENT INVENTION

Figure 1:
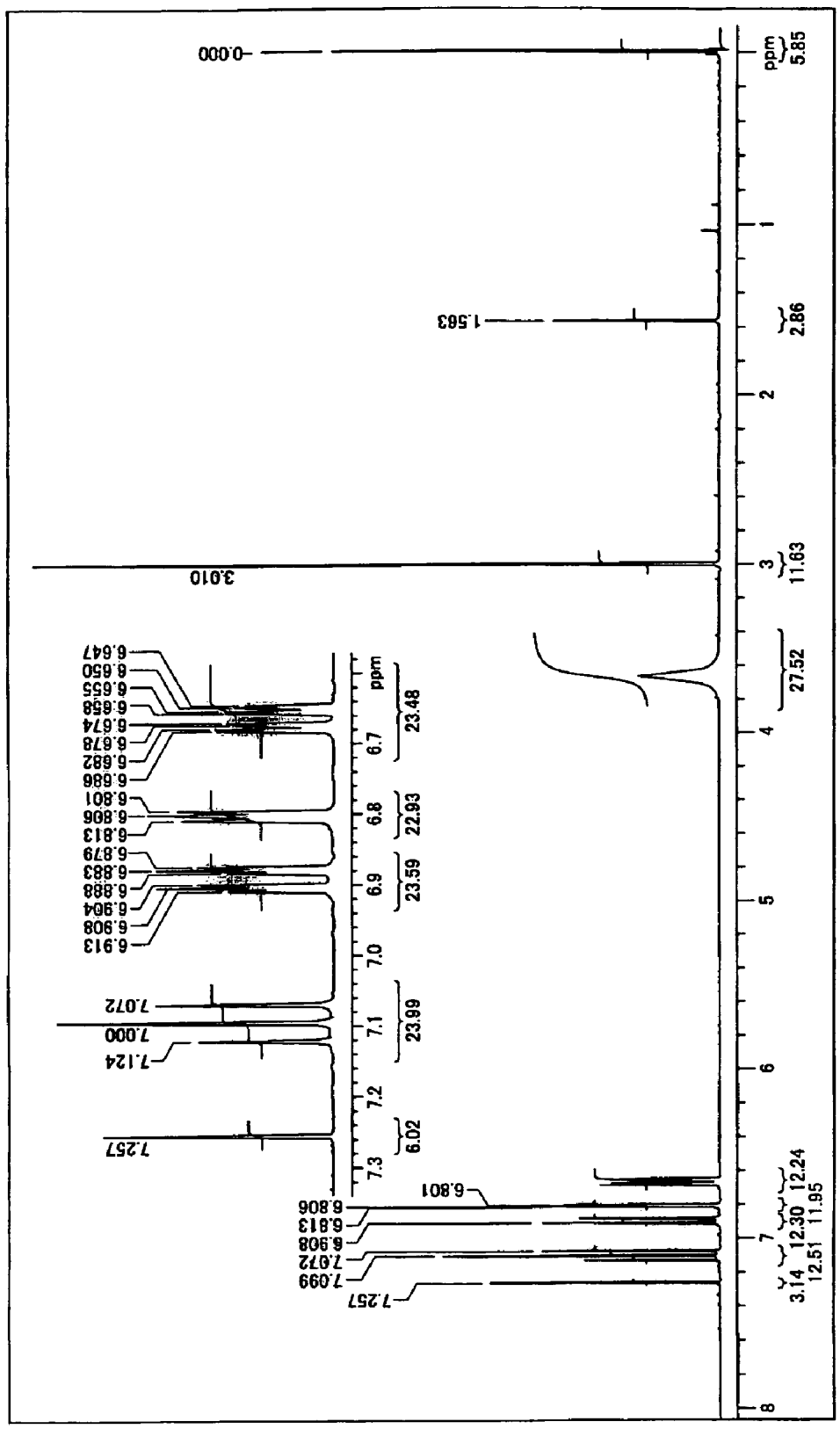
FIG. 1 is a $^1$H-NMR chart of 3-aminophenylacetylenes obtained in Example 1.

First, a 3-haloaniline compound represented by formula (1) will be described.

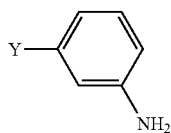

Formula (1)

wherein, Y represents a halogen atom. Examples of the halogen atom include a fluorine atom, a chlorine atom, a bromine atom, or an iodine atom, preferably a chlorine atom, a bromine atom, or an iodine atom, more preferably a bromine atom, or an iodine atom, and further preferably a bromine atom.

Then, an acetylene compound represented by formula (2) will be described.

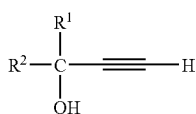

Formula (2)

wherein, $R^1$ and $R^2$ each independently represent a hydrogen atom, a substituted or unsubstituted alkyl group having 1 to 6 carbon atoms, a substituted or unsubstituted cycloalkyl group having 3 to 6 carbon atoms or an aryl group having 6 to 12 carbon atoms. The alkyl, cycloalkyl and aryl group represented by $R^1$ and $R^2$ may have at least one substituent. Examples of the substituent include an alkyl group, a cycloalkyl group, an aryl group, a halogen atom, a nitro group, a cyano group, a hydroxyl group, an alkoxy group, an aryloxy group, an alkylthio group, an arylthio group, an amino group, an alkylamino group, an arylamino group, an acyl group, an acylamino group, a sulfonamide group, a carbamoyl group, a sulfamoyl group, an alkoxycarbonyl group, an aryloxycarbonyl group, a heterocyclic group, and the like.

When $R^1$ and $R^2$ each represent an alkyl group having 1 to 6 carbon atoms or a cycloalkyl group having 3 to 6 carbon atoms, they may be any of straight chain, branched, and cyclic groups. Examples thereof may include methyl, ethyl, n-propyl, isopropyl, isobutyl, t-butyl, n-hexyl, cyclopropyl, cyclopropylmethyl, cyclobutyl, and cyclohexyl, preferably methyl, ethyl, isobutyl, and cyclopropyl. Alternatively, $R^1$ and $R^2$ may combine with each other to form a ring. The ring is preferably a 3- to 7-membered ring, and preferably an alicyclic ring. Examples thereof may include a cyclopropane ring, a cyclopentane ring, and a cyclohexane ring.

When $R^1$ and $R^2$ each represent an aryl group having 6 to 12 carbon atoms, as the aryl group, a substituted or unsubstituted aromatic hydrocarbon group may be mentioned. Specific examples of the aryl group may include phenyl, 1-naphthyl, 2-naphthyl, p-tolyl, and 2,4,6-trimethylphenyl(mesityl), preferably phenyl, 1-naphthyl, and p-tolyl, more preferably phenyl and p-tolyl, and particular preferably phenyl.

The case where $R^1$ and $R^2$ both are alkyl groups having 1 to 6 carbon atoms is preferred. The case where $R^1$ and $R^2$ both are methyl groups is more preferred.

Preferred examples of the acetylene compound represented by formula (2) will be shown below, but the present invention is not limited thereto.

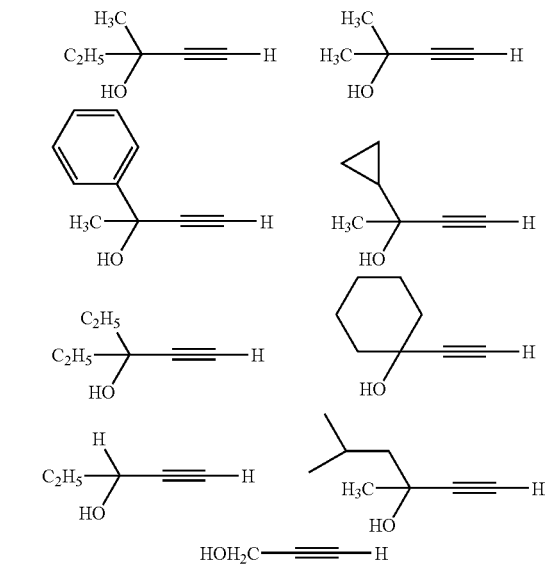

The acetylene compounds represented by formula (2) can be obtained by the processes described in the literature such as *J. Org. Chem.*, vol. 63, p. 3515 (1998).

Then, the aniline compounds represented by formula (4) will be described.

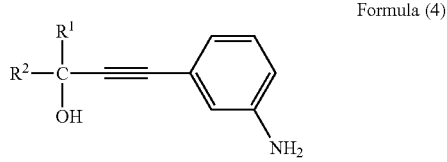

Formula (4)

In the formula (4), $R^1$ and $R^2$ have the same definitions as described in relation to formula (2), and the preferred ranges thereof are also the same. Further, $R^1$ and $R^2$ may combine with each other to form a ring, and the preferred range of the ring is also the same as described in relation to formula (2).

Preferred examples of the aniline compound represented by formula (4) will be shown below, but the present invention is not limited thereto.

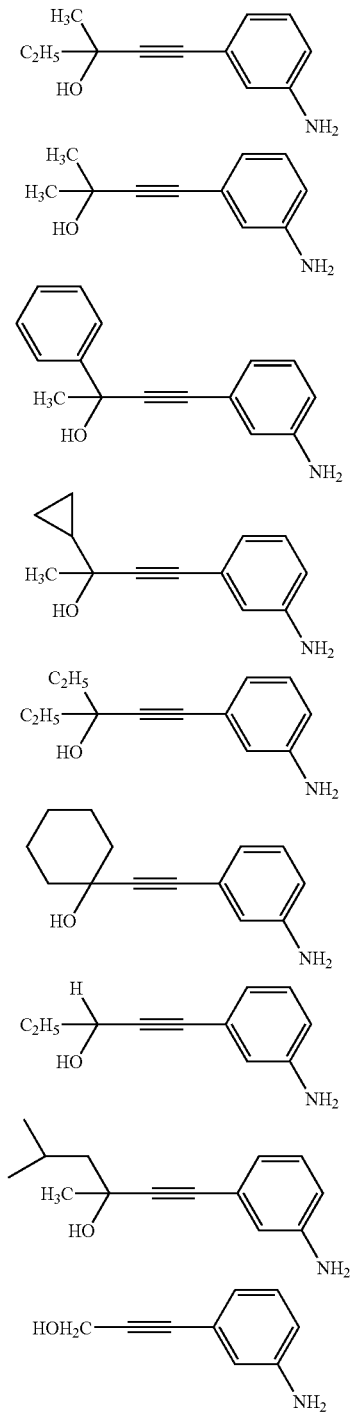

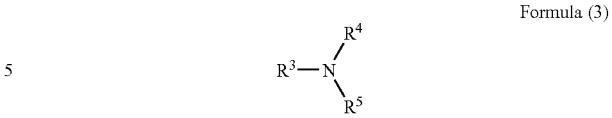

Formula (3)

wherein, $R^3$ represents a hydrogen atom, a substituted or unsubstituted alkyl group having 1 to 6 carbon atoms or a substituted or unsubstituted cycloalkyl group having 3 to 6 carbon atoms.

The alkyl and cycloalkyl group represented by $R^3$ may have at least one substituent. Examples of substituent may include the same those mentioned for the alkyl and cycloalkyl group represented by $R^1$ and $R^2$.

When $R^3$ represents an alkyl group having 1 to 6 carbon atoms, preferably 1 to 4 carbon atoms, or a cycloalkyl group having 3 to 6 carbon atoms, it may be any of straight chain, branched, and cyclic groups. Examples thereof may include methyl, ethyl, n-propyl, isopropyl, n-butyl, isobutyl, t-butyl, cyclopropyl, and cyclopropylmethyl.

$R^3$ is preferably a hydrogen atom, methyl, ethyl, n-propyl, isopropyl, n-butyl, or isobutyl.

$R^4$ and $R^5$ each independently represent an alkyl group having 1 to 6 carbon atoms, preferably 1 to 4 carbon atoms, a cycloalkyl group having 3 to 6 carbon atoms or an aryl group having 6 to 12 carbon atoms. Each alkyl group having 1 to 6 carbon atoms or cycloalkyl group having 3 to 6 carbon atoms represented by $R^4$ and $R^5$ may be unsubstituted or may have at least one substituent. As the substituent, a hydroxyl group, a methyl group, a methoxy group, an ethoxy group, a cyano group, a methoxycarbonyl group, an ethoxycarbonyl group, a phenoxy group, and the like are mentioned, preferably, a methyl group, a methoxy group, an ethoxy group, a cyano group, a phenoxy group, and the like, and more preferably, a methyl group, a methoxy group, an ethoxy group, and the like, and still more preferably, a methoxy group, an ethoxy group, and the like.

Each alkyl group having 1 to 6 carbon atoms or cycloalkyl group having 3 to 6 carbon atoms represented by $R^4$ and $R^5$ may be any of straight chain, branched, and cyclic groups. Examples thereof may include methyl, ethyl, n-propyl, isopropyl, n-butyl, isobutyl, t-butyl, cyclopropyl, and cyclopropylmethyl. Methyl, ethyl, n-propyl, isopropyl, n-butyl, and isobutyl are preferred.

The aryl groups having 6 to 12 carbon atoms represented by $R^4$ and $R^5$ may be phenyl, 1-naphthyl, 2-naphthyl, and the like, phenyl and 1-naphthyl are preferred, and phenyl is particularly preferred.

Each aryl group having 6 to 12 carbon atoms represented by $R^4$ and $R^5$ may be unsubstituted, or may have at least one substituent. As the substituents, a methyl group, an ethyl group, a nitro group, a methoxy group, a chlorine atom, a fluorine atom, and the like may be mentioned, preferably, a methyl group, a nitro group, a methoxy group, and a chlorine atom, and more preferably a methyl group, a nitro group, and the like.

$R^4$ and $R^5$ may combine with each other to form a ring. The ring may be an alicyclic ring or a hetero ring, and may be an aromatic ring or an unsaturated ring other than an aromatic ring, and is preferably a 3- to 7-membered ring, and more preferably a 5- or 6-membered ring. Examples of the preferred ring include a nitrogen-containing 5-membered ring Then, the respective steps a) to c) in the process of the present invention, and the reaction or the operational conditions thereof will be described in details.

In the step (a) in the process of the present invention, a 3-haloaniline compound represented by formula (1) is reacted with an acetylene compound represented by formula (2) in the presence of a palladium compound, a copper compound, and an amine compound represented by formula (3) to obtain an aniline compound represented by formula (4).

(e.g., a pyrrolidine ring) or a 6-membered ring (e.g., a piperidine ring), or an oxygen atom-containing 6-membered ring (e.g., a morpholine ring).

Specific examples of the amine compound represented by formula (3) may include diethylamine, diisopropylamine, piperidine, pyrrolidine, N-methylmorpholine, N-methylpiperidine, triethylamine, tri-n-propylamine, tri-n-butylamine, diisopropylethylamine, N,N-dimethylaniline, and N,N-diethylaniline. Among them, N,N-dimethylaniline, N,N-diethylaniline, N-methylaniline, N-ethylaniline, tri-n-butylamine, tri-n-propylamine, triethylamine, diisopropylethylamine, diethylamine, diisopropylamine, N-methylmorpholine, N-methylpiperidine, dibutylamine, and the like are preferred, and N,N-dimethylaniline, N,N-diethylaniline, N-methylaniline, tri-n-butylamine, triethylamine, diisopropylethylamine, diethylamine, diisopropylamine, N-methylmorpholine, N-methylpiperidine, and dibutylamine are more preferred. N,N-dimethylaniline, N,N-diethylaniline, tri-n-butylamine, triethylamine, diisopropylethylamine, diisopropylamine, N-methylmorpholine, and N-methylpiperidine are particularly preferred. Most preferred amine compounds are N,N-dimethylaniline, N,N-diethylaniline, triethylamine, diisopropylethylamine, diisopropylamine, and N-methylmorpholine, or a combined system of two or three amine compounds selected from these.

In the present invention, it is not necessary to use expensive strong bases such as diazabicycloundecane and 1,1,3,3-tetramethylguanidine.

The amount of the amine compound represented by formula (3) is preferably in the range of 1.0 to 20.0 equivalents, more preferably 2.0 to 10 equivalents, and further preferably 2.5 to 6.0 equivalents based on the amount of the 3-haloaniline compound represented by formula (1).

As the palladium compound in the step a), a divalent or zero-valent palladium compound may be used.

Preferred examples of the divalent or zero-valent palladium compound are palladium compounds represented by $PdX_2$ coordinated to a phosphine compound, wherein X represents a chloride ion, a bromide ion, an iodide ion, an acetic acid ion, acetyl acetonate, or dibenzyl acetonate.

Further preferred are palladium compounds represented by formula (P1), (P2), or (P3) described hereinafter.

$L_2PdX_2$ <span style="float:right">Formula (P1):</span>

In formula (P1), L represents a monodentate phosphine compound, and is preferably a phosphine compound represented by $P(R^6)(R^7)(R^8)$ in which $R^6$ to $R^8$ each independently represent a hydrocarbon group such as an aryl group or an alkyl group, and at least two of $R^6$ to $R^8$ may combine with each other to form a ring. Specific examples of $R^6$ to $R^8$ may include methyl, ethyl, propyl, n-butyl, tert-butyl, cyclohexyl, ethylhexyl, octyl, benzyl, o-toluyl, m-toluyl, phenyl, and naphthyl. Preferred are n-butyl, cyclohexyl, octyl, o-toluyl, phenyl, and naphthyl, more preferred are cyclohexyl, octyl, o-toluyl, and phenyl, and further preferred are o-toluyl and phenyl.

X represents a chloride ion, a bromide ion, an iodide ion, an acetic acid ion, acetyl acetonate, or dibenzyl acetonate. Preferred are a chloride ion, an acetic acid ion, or acetylacetonate.

Specific examples of formula (P1) may include bis(triphenylphosphine) palladium (II) dichloride.

$(L-L)PdX_2$ <span style="float:right">Formula (P2):</span> wherein in formula (P2), (L–L) represents a bidentate phosphine compound or a bidentate nitrogen compound.

Examples of the bidentate phosphine compound may include bis(diphenylphosphino)methane, 1,2-bis(diphenylphosphino)ethane, 1,2-bis(diphenylphosphino)ethylene, 1,3-bis(diphenylphosphino)propane, 1,4-bis(diphenylphosphino)butane, and 1,1'-(diphenylphosphino)ferrocene.

As the bidentate nitrogen compound, 1,10-phenanthroline is preferably exemplified. X has the same definition as for X in formula (P1), and the preferred range thereof is also the same.

$PdL_4$ <span style="float:right">Formula (P3):</span>

In formula (P3), L has the same definition as for L in formula (P1), and the preferred range thereof is also the same.

In the palladium coupling reaction of aryl halide and an acetylene compound conventionally reported, as is often the case, a palladium compound represented by formula (P1), for example, bis(triphenylphosphine)palladium (II) dichloride or the like is used as a catalyst (see, for example, JP-A-10-36325 or *Synthesis*, p. 364 (1981)). However, the palladium compound represented by formula (P1) is very expensive.

Under such circumstances, in the process of the present invention, the palladium compound represented by formula (P1) is mixed in the reaction system, and used. Namely, a palladium compound represented by $PdX_2$ and a phosphine compound coordinating thereto are added in the reaction system so as to produce a palladium compound represented by formula (P1) in the same reaction system. This allows preparation to be done using inexpensive palladium compounds represented by $PdX_2$ and a phosphine compound.

Specifically, examples of the phosphine compound to be combined with the palladium compound represented by $PdX_2$ may include monodentate phosphine compounds represented by $P(R^6)(R^7)(R^8)$, and bidentate phosphine compounds. The specific examples and the preferred range are the same as those described previously. More preferred phosphine compounds are tri(o-toluyl)phosphine and triphenylphosphine. $PdX_2$ also has the same definitions as described in relation to formula (P1). However, palladium (II) acetate is particularly preferred.

The amount of each palladium compound represented by formulae (P1) to (P3) is preferably in the range of $1.0 \times 10^{-8}$ to $5.0 \times 10^{-2}$ equivalent, and more preferably $1.0 \times 10^{-6}$ to $5.0 \times 10^{-3}$ equivalent based on the amount of a 3-haloaniline compound represented by formula (1).

Even when the amount of palladium compound exceeds this range, yields of the final products and isolation yield are not so improved, although the reaction rate is improved. This rather leads to an increase in coloration of the reaction mixture/product, or an increase in cost, and, therefore, causes a hindrance in preparation on an industrial scale. Conversely, when the amount of the palladium compound to be used is equal to, or less than this range, the reaction rate is remarkably reduced.

Also, when a palladium compound represented by $PdX_2$ and a phosphine compound are added in the reaction system to prepare a palladium compound coordinated to a phosphine compound represented by formula (P1) or (P2), the amount of the phosphine compound to be used is in the range of preferably 1.0 to 100 equivalents, more preferably 1.0 to 40 equivalents, further preferably 2.0 to 25 equivalents, and in particular preferably 4.0 to 15 equivalents, based on the amount of the palladium compound represented by $PdX_2$.

Even when the compound is used largely excessively in an amount exceeding the range, reaction rate, product yield, and desired product are not so affected. Conversely, when the phosphine compound is too excessively used, the subsequent removing operation becomes complicated. This rather leads to an increase in amount of waste material or an increase in cost, and hence, causes a hindrance in preparation on an industrial scale.

The copper compound in the step a) is preferably a monovalent copper compound.

Specific examples of the copper (I) compound preferably include copper (I) chloride, copper (I) bromide, copper (I) iodide, copper (I) acetate, and copper (I) cyanide. More preferred are copper (I) chloride, copper (I) bromide, and copper (I) iodide, and two or more coppers of these can also be used in combination.

The amount of the copper compound to be used is in the range of preferably $1.0 \times 10^{-5}$ to $5.0 \times 10^{-1}$ equivalent, more preferably $1.0 \times 10^{-4}$ to $5.0 \times 10^{-1}$ equivalen and further preferably $1.0 \times 10^{-3}$ to $2.0 \times 10^{-1}$ equivalent based on the amount of the 3-haloaniline compound represented by formula (1).

In the step a), a quaternary ammonium salt can also be further used.

Examples of the quaternary ammonium salts include tetraethylammonium bromide, tetraethylammonium iodide, benzyl tributylammonium chloride, benzyl tributylammonium iodide, benzyl triethylammonium bromide, benzyl triethylammonium chloride, benzyl trimethylammonium bromide, benzyl trimethylammonium chloride, and the like. The amount of the quaternary ammonium salt to be used is preferably in the range of $1.01 \times 10^{-2}$ to $5.0 \times 10^{-1}$ equivalent based on the amount of the 3-haloaniline compound represented by formula (1).

An amount of the acetylene compound represented by formula (2) to be reacted is preferably in an amount of 0.8 to 3.0 equivalents, more preferably in an amount of 1.0 to 2.0 equivalents, and further preferably 1.1 to 1.5 equivalents based on the amount of 3-haloaniline compound represented by formula (1).

The reaction solvent in the step a) is not particularly limited so long as it does not pose a problem in the reaction operation such as stirring defect due to precipitation and the like of reaction substrate/reaction intermediate/reaction product, does not hinder the proceeding of the reaction, and it does not affect adversely on the reactions owing to the decomposition under the reaction conditions of the present invention. Examples thereof may include alcohol type solvents such as ethanol, 2-propanol, 1-butanol, and ethylene glycol, aprotic polar solvents such as N,N-dimethylformamide, N,N-dimethylacetamide, N-methylpyrrolidone, sulfolane, dimethylsulfoxide, and N,N-dimethyl imidazolidinone, ether type solvents such as diisopropyl ether, methyl-t-butyl ether, 1,2-dimethoxy ethane, tetrahydrofuran, and anisole, ester type solvents such as ethyl acetate and n-butyl acetate, aliphatic hydrocarbon solvents such as hexane, heptane, and decane, aromatic hydrocarbon solvents such as toluene, xylene (which may be any of the o-form, the m-form, or the p-form, or a mixture of these in a given ratio), mesitylene, ethylbenzene, t-butylbenzene, isopropylbenzene (cumene), and chlorobenzene, acetonitrile, and propionitrile. Among them, acetonitrile, tetrahydrofuran, ethyl acetate, toluene, ethylbenzene, heptane, decane, N,N-dimethylformamide, N,N-dimethylacetamide, N-methylpyrrolidone, sulfolane, and dimethylsulfoxide are preferred, and acetonitrile, tetrahydrofuran, ethyl acetate, toluene, N,N-dimethylformamide, N,N-dimethylacetamide, N-methylpyrrolidone, and dimethylsulfoxide are more preferred.

These solvents may be used alone, or two or more solvents may be used in combination. Alternatively, the amine compound represented by formula (3) described previously can also be used as a solvent.

When a solvent is used, it is used in an amount of preferably 0.1 to 100 kg, more preferably 0.5 to 10 kg, and further preferably 0.8 to 5 kg per kilogram of a 3-haloaniline compound represented by formula (1).

The reaction temperature of the step a) is within the range of generally 20 to 200° C., preferably 50 to 150° C., and more preferably 60 to 130° C. The reaction time varies depending on charging amount and reaction temperature, but it is generally in the range of 0.5 to 20 hours, and more preferably 3 to 10 hours. For the reaction, it is preferable to effect under an inert atmosphere of an argon or nitrogen flow, or the like.

Further, the order of addition of a 3-haloaniline compound represented by formula (1), an acetylene compound represented by formula (2), and a palladium compound, a copper compound and an amine compound represented by formula (3) is not particularly limited. However, it is preferable that an acetylene compound represented by formula (2) is added dropwise to a mixture of a 3-haloaniline compound represented by formula (1), and a palladium compound, a copper compound and an amine compound represented by formula (3) with heating at the reaction temperature of the range described above from the viewpoint of controlling the reaction in which the acetylene compound represented by formula (2) is converted to a diyne compound by the oxidation reaction.

Then, the step b) will be described.

In the step b), an aniline compound represented by formula (4) is precipitated in the form of a crystal, which is isolated by solid liquid separation.

After the reaction of the step (a), in order to isolate the resulting reaction product, first, the insoluble materials including the salt compounds formed as by-products and the catalyst in the reaction system are removed by solid/liquid separation. The process of solid/liquid separation is not particularly limited, and any of known process can be applied.

Then, the reaction mixture from which the insoluble materials have been removed is concentrated, or diluted with an appropriate organic solvent. Then, liquid/liquid separation (so-called separating operation), and if required, a chemical engineering operation such as concentration are carried out. Subsequently, crystallization is carried out from an appropriate solvent system.

Examples of the solvent system for crystallizing the aniline compound represented by formula (4) may include alcohol type solvents such as ethanol and 2-propanol, ether type solvents such as diisopropyl ether and methyl-t-butyl ether, ester type solvents such as ethyl acetate and n-butyl acetate, acetonitrile, and propionitrile, or mixed systems of these organic solvents and nonpolar organic solvents (specifically, aliphatic hydrocarbon solvents such as hexane and heptane, and aromatic hydrocarbon solvents such as toluene). As the crystallizing solvent, acetonitrile alone, propionitrile alone, toluene/2-propanol mixed system, hexane/2-propanol mixed system, heptane/2-propanol mixed system, heptane/methyl-t-butyl ether mixed system, hexane/acetonitrile mixed system, or the like may be mentioned.

The amount of the crystallizing solvent is generally in a range of 3 to 50 times by volume, and preferably 3 to 20 times by volume relative to kilogram of the aniline compound represented by formula (4).

The temperature for precipitating the crystal is 50° C. or less, and preferably 5 to 30° C.

The crystallized aniline compound represented by formula (4) can be easily isolated by the conventional solid/liquid separation, and therefore, impurities and colored components can be removed efficiently from the reaction step to obtain an aniline compound represented by formula (4) with a high purity.

Then, the step c) will be described.

In the step c), the resulting aniline compound represented by formula (4) is reacted with a base to obtain 3-aminophenylacetylene represented by formula (5).

The aniline compound represented by formula (4) has a skeleton in which a terminal acetylene compound and a ketone compound are aldol condensed. Thus, by performing a base treatment, it is possible to regenerate a terminal acetylene structure by a retro-aldol reaction. The technique is known in terms of synthetic chemistry. For example, the processes described in JP-A-10-36325, *J. Org. Chem.*, vol. 44, p. 1233 (1979), or *Synthesis*, p. 364 (1981) are applied thereto as typical examples.

The reaction solvent for use in the reaction of the aniline compound represented by formula (4) with a base to produce 3-aminophenylacetylene is not particularly limited so long as it does not pose a problem in the reaction operation such as stirring defect due to precipitation and the like, and it is stable under the reaction conditions of the invention. Examples thereof may include ether type solvents such as diisopropyl ether, methyl-t-butyl ether, 1,2-dimethoxy ethane, tetrahydrofuran, and anisole, aliphatic hydrocarbon solvents such as hexane, heptane, and decane, aromatic hydrocarbon solvents such as toluene, xylene (which may be any of o-form, m-form, or p-form, or a mixture of these in a given ratio), mesitylene, ethylbenzene, t-butylbenzene, isopropylbenzene (cumene), and chlorobenzene.

The reaction solvent is used in an amount of preferably 2 to 50 L, more preferably 2.5 to 20 L, and further preferably 3 to 10 L relative to kilogram of the aniline compound represented by formula (4).

As the base in the step c), a hydroxide, a carbonate, or an alkoxide of an alkali metal, and a hydroxide, a carbonate, or an alkoxide of an alkaline-earth metal, and the like. Preferred are an alkali metal hydroxide, an alkali metal alkoxide, an alkaline-earth metal hydroxide, and an alkaline-earth metal alkoxide. Specific examples of the base include sodium hydroxide, potassium hydroxide, sodium methoxide, potassium methoxide, sodium ethoxide, sodium-t-butoxide, magnesium hydroxide, barium hydroxide, and magnesium methoxide.

Among them, from the viewpoints of mass production suitability on an industrial scale, availability, price, and the like, alkali metal hydroxides such as sodium hydroxide and potassium hydroxide are particularly preferred. They may be used in the form of a flake, or in the form of a pellet, or may be used in the form of an aqueous solution with a given concentration. When they are used in the form of an aqueous solution, the reaction medium is of a two-phase system including an organic solvent and water. However, even in the two-phase system medium, the conversion from the aniline compound represented by formula (4) to 3-aminophenylacetylene proceeds with ease. This is one of preferred embodiments of the process of the invention.

The base in the step c) is used in an amount of preferably 0.05 to 3.0 equivalents, more preferably 0.1 to 2 equivalents, and further preferably 0.2 to 1.2 equivalents based on the amount of the aniline compound represented by formula (4).

The reaction temperature in the step c) is within the range of generally 60 to 200° C., preferably 60 to 150° C., and more preferably 70 to 140° C.

The reaction time varies depending on charging amount and reaction temperature. However, it is within the range of generally 0.5 to 8 hours, and more preferably 1 to 6 hours.

Preferably, the reaction is carried out under an inert atmosphere of an argon or nitrogen flow, and the ketone compound as the byproduct in the reaction is removed from the system.

After the completion of the reaction, an organic layer including the desired 3-aminophenylacetylene dissolved therein is washed with water, and concentrated. As a result, it is possible to obtain 3-aminophenylacetylene with ease. The 3-aminophenylacetylene thus obtained has such a purity as to be usable in the subsequent steps without further purification. If required, it can also be purified by distillation, or by undergoing salt formation according to the process described in JP-A-10-36325, to be used in the subsequent steps.

The 3-aminophenylacetylene compounds represented by formula (5), obtained according to the invention are useful as synthetic intermediates for thermosetting resins, nonlinear optical materials, luminescent materials, light responsive devices, adhesives, pharmaceutical and agricultural chemicals, or the like, and crosslinking agents.

Also, in the process of the present invention, it is possible to prepare a 3-aminophenylacetylene compound represented by formula (5) without effecting a preparation of a special catalyst, and without using a reaction agent which is undesirable for the environment. Therefore, the process of the present invention is very excellent in productivity. Accordingly, it is possible to economically prepare 3-aminophenylacetylene represented by formula (5) on an industrial scale.

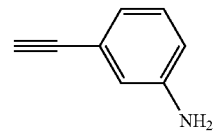

Formula (5)

Hereinafter, the present invention will be described with reference to embodiments, but is not limited thereto.

EXAMPLES

Example 1

(Synthesis of 3-aminophenylacetylene Via Intermediate 1)

Synthetic reaction scheme is as follows:

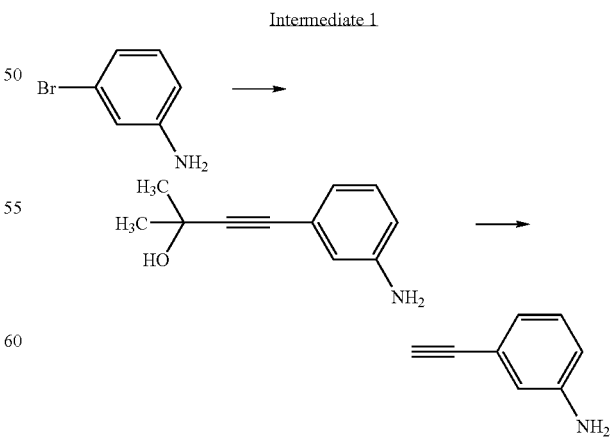

To a mixture of 3-bromoaniline (172 g), triphenylphosphine (8.5 g), palladium (II) acetate (600 mg), copper (I)

iodide (1.2 g), and triethylamine (500 g), 2-methyl-3-butyn-2-ol (100 g) was added dropwise with heating and stirring under reflux conditions. The reaction mixture was stirred for 7 hours, and then, cooled, and the precipitated insoluble components were filtered off. The filtrate was concentrated to obtain a residue. To the residue, 2-propanol (150 ml) and hexane (400 ml) were added, and dissolved with heating. The mixture was then cooled to 20° C. with stirring, and thus, a crystal was precipitated.

The crystallized solution was cooled to 10° C., and then the crystal was collected by filtration, and washed and dried, resulting in 132 g of an intermediate 1 in the form of a light-brown needle crystal. The yield was 75% based on 3-bromoaniline. The analysis results of the resulting intermediate 1 are as follows:

Melting point: 117.2 to 118.0° C.

$^{1}$H-NMR (CDCl$_3$, TMS) and mass spectrum data were in agreement with the values described in *J. Org. Chem.*, vol. 44, p. 1233 (1979).

Then, a mixture of the intermediate 1 (105 g), sodium hydroxide (7 g), and toluene (250 ml) was heated to reflux under a nitrogen flow for 3 hours. The reaction mixture was cooled to room temperature, and then filtered. The filtrate was then washed with an aqueous solution of disodium ethylenediaminetetraacetate (EDTA-disodium salt), and then with water. Then, toluene was distilled off. The residue was distilled, resulting in 62 g of 3-aminophenylacetylene in the form of a colorless liquid. The yield was 88%. Analysis results of the resulting 3-aminophenylacetylene in the form of a colorless liquid are as follows:

Boiling point: 128 to 132° C./5 mmHg
GC purity: 99.2%
MS: m/z 117 (M$^+$), 89, 69, 59
$^{1}$H-NMR (CDCl$_3$, TMS): the chart of the measurement results is shown in FIG. 1.

The GC measuring conditions are as follows:
Column: Chrompack WCOT FUSED SILICA CP-SIL 8CB for AMINES 0.25 mm×30 m
Carrier gas: helium, 50 kPa
Detection: FID
Temperature: 130° C. (20 minutes)→180° C. (elevated temperature rate 10° C./min)

Example 2

(Synthesis of 3-aminophenylacetylene Via Intermediate 1)

The synsthetic reaction scheme is the same as described in Example 1.

A mixture of 3-bromoaniline (172 g), triphenylphosphine (8.5 g), palladium (II) acetate (600 mg), copper (I) iodide (1.2 g), tetra-n-butylammonium bromide (9 g), 2-methyl-3-butyn-2-ol (100 g), and triethylamine (500 g), was stirred under reflux conditions for 6 hours. The reaction mixture was cooled, and then the precipitated insoluble components were filtered off. The filtrate was concentrated, and diluted with ethyl acetate. It was then washed with an aqueous solution of disodium ethylenediaminetetraacetate (EDTA—disodium salt), and then with water, and concentrated. The residue was crystallized from a mixed system of 2-propanol/hexane (volume ratio 1/3), and the precipitated crystal was collected by filtration, and washed and dried, resulting in 128 g of an intermediate 1 in the form of a light-brown needle crystal. The yield was 73.1% based on 3-bromoaniline.

The values on physical property were in agreement with the values described in Example 1 and J. Org. Chem., vol. 44, 1233 page (1979).

According to the same manner as described in Example 1, 3-aminophenylacetylene in the form of a colorless liquid was obtained. The yield was 87%.

The GC purity was 99.3%. The measurement conditions were set to be the same as the measurement conditions described in Example 1.

Also, various spectrum data were in agreement with the data obtained in Example 1.

Example 3

(Synthesis of 3-aminophenylacetylene Via Intermediate 1)

The synsthetic reaction scheme is the same as described in Example 1.

The mixture of the intermediate 1 (50 g) synthesized in Example 2, toluene (150 ml), and a sodium hydroxide aqueous solution (sodium hydroxide 5 g/water 50 ml), was heated with stirring under a nitrogen flow at 90° C. for 3 hours. The reaction mixture was cooled to room temperature, and then, the organic layer was collected, and washed with water. Then, toluene was distilled off. The residue was distilled, resulting in 29 g of 3-aminophenylacetylene in the form of a colorless liquid. The yield was 83%.

The GC purity was 99.0%. The measurement conditions were set to be the same as the measurement conditions described in Example 1.

Also, various spectrum data were in agreement with the data obtained in Example 1.

As clear from Examples described above, the process of the present invention does not require the preparation of a special catalyst and the use of a reaction agent which is undesirable for the environment, and does not require a complicated operation as in chromatography. The purity of the target substance is also high, and it is possible to economically prepare 3-aminophenylacetylene on an industrial scale.

In accordance with the present invention, it is possible to provide a process for preparing 3-aminophenylacetylenes, which can minimize waste material, and can be carried out economically on an industrial scale without using compounds and solvents which are undesirable for the environment.

All publications, patent applications, and technical standards mentioned in this specification are herein incorporated by reference to the same extent as if each individual publication, patent application, or technical standard was specifically and individually indicated to be incorporated by reference.

What is claimed is:

1. A process for preparing a 3-aminophenylacetylene compound represented by formula (5), comprising:
   a) reacting a 3-haloaniline compound represented by formula (1) with an acetylene compound represented by formula (2) in the presence of a palladium compound, a copper compound, and an amine compound represented by formula (3) to form an aniline compound represented by formula (4);
   b) precipitating the resultant aniline compound represented by formula (4) in the form of a crystal, and isolating it by solid/liquid separation; and
   c) reacting the aniline compound represented by formula (4) obtained in the above b) with a base to obtain 3-aminophenylacetylene represented by formula (5):

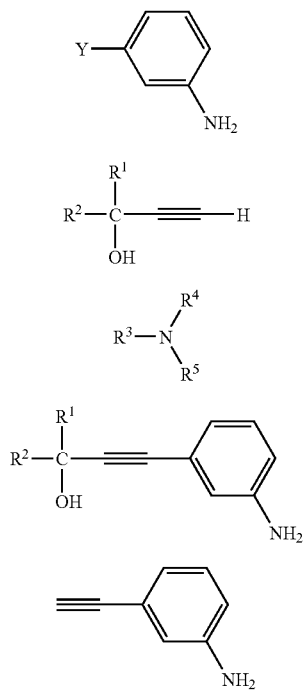

wherein, in formulae (1) to (4), Y represents a halogen atom; $R^1$ and $R^2$ each independently represent a hydrogen atom, a sustituted or unsubstituted alkyl group having 1 to 6 carbon atoms, a substituted or unsubstituted cycloalkyl group having 3 to 6 carbon atoms, or a substituted or unsubstituted aryl group having 6 to 12 carbon atoms, or $R^1$ and $R^2$ may combine with each other to form a ring; $R^3$ represents a hydrogen atom, a substituted or unsubstituted alkyl group having 1 to 6 carbon atoms or a substituted or unsubstituted cycloalkyl group having 3 to 6 carbon atoms; and $R^4$ and $R^5$ each independently represent a substituted or unsubstituted alkyl group having 1 to 6 carbon atoms, a substituted or unsubstituted cycloalkyl group having 3 to 6 carbon atoms or a substituted or unsubstituted aryl group having 6 to 12 carbon atoms, or $R^4$ and $R^5$ may combine with each other to form a ring.

2. The process according to claim 1, wherein the amine compound represented by formula (3) is selected from the group consisting of diethylamine, diisopropylamine, piperidine, pyrrolidine, N-methylmorpholine, N-methylpiperidine, triethylamine, tri-n-propylamine, tri-n-butylamine, diisopropylethylamine, N,N-dimethylaniline, and N,N-diethylaniline.

3. The process according to claim 1, wherein the amount of the amine compound represented by formula (3) is within the range of 1.0 to 20.0 equivalent based on the amount of the 3-haloaniline compound represented by formula (1).

4. The process according to claim 1, wherein the palladium compound is a palladium compound represented by $PdX_2$ coordinated to a phosphine compound, wherein X represents a chloride ion, a bromide ion, an iodide ion, an acetic acid ion, acetyl acetonate, or dibenzyl acetonate.

5. The process according to claim 4, wherein the palladium compound is a palladium compound represented by formula (P1), (P2), or (P3):

$L_2PdX_2$     Formula (P1)

$(L-L)PdX_2$     Formula (P2)

$PdL_4$     Formula (P3)

wherein in formulae (P1) and (P3), L represents a monodentate phosphine compound represented by $P(R^6)(R^7)(R^8)$ in which $R^6$ to $R^8$ each independently represent a hydrocarbon group of an aryl group or an alkyl group, and at least two of $R^6$ to $R^8$ may combine with each other to form a ring; and in formulae (P1) and (P2), X represents a chloride ion, a bromide ion, an iodide ion, an acetic acid ion, acetyl acetonate, or dibenzyl acetonate; and in formula (P2), (L-L) represents a bidentate phosphine compound or a bidentate nitrogen compound.

6. The process according to claim 5, wherein the amount of each palladium compound represented by formulae (P1), (P2) or (P3) is within the range of $1.0 \times 10^{-8}$ to $5.0 \times 10^{-2}$ equivalent based on the amount of a 3-haloaniline compound represented by formula (1).

7. The process according to claim 4, wherein the palladium compound represented by $PdX_2$ and the phosphine compound coordinating thereto are added in the reaction system to effect the reaction.

8. The process according to claim 7, wherein the amount of the phosphine compound is within the range of 1.0 to 100 equivalent based on the amount of the palladium compound represented by $PdX_2$.

9. The process according to claim 1, wherein the copper compound is one or more monovalent copper compounds selected from the group consisting of copper (I) chloride, copper (I) bromide, copper (I) iodide, copper (I) acetate, and copper (I) cyanide.

10. The process according to claim 1, wherein the reaction temperature of step a) is within the range of 20 to 200° C.

11. The process according to claim 1, wherein the solvent system for crystallizing the aniline compound represented by formula (4) comprises an organic solvent selected from the group consisting of alcohol type solvents, ether type solvents, ester type solvents, acetonitrile, and propionitrile used alone, or a mixture of one or more of these organic solvents with a nonpolar organic solvent selected from the group consisting of aliphatic hydrocarbon solvents and aromatic hydrocarbon solvents.

12. The process according to claim 1, wherein the temperature for precipitating the crystal is 50° C. or less.

13. The process according to claim 1, wherein the base in step c) is selected from the group consisting of a hydroxide, a carbonate, or an alkoxide of an alkali metal, and a hydroxide, a carbonate, or an alkoxide of an alkaline-earth metal.

14. The process according to claim 1, wherein the amount of the base is within the range of 0.05 to 3.0 equivalent based on the amount of the aniline compound represented by formula (4).

15. The process according to claim 1, wherein the reaction temperature in step c) is within the range of 60 to 200° C.

16. A process for preparing a 3-aminophenylacetylene compound represented by formula (5), comprising:
   a) reacting a 3-haloaniline compound represented by formula (1) with an acetylene compound represented by formula (2) in the presence of a palladium compound, a copper compound, a quaternary ammonium salt, and an amine compound represented by formula (3) to form an aniline compound represented by formula (4);
   b) precipitating the resultant aniline compound represented by formula (4) in the form of a crystal, and isolating it by solid/liquid separation; and c) reacting the aniline compound represented by formula (4) obtained in the above b) with a base to obtain 3-aminophenylacetylene represented by formula (5):

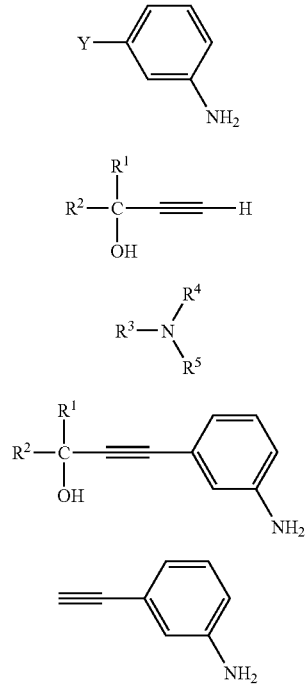

Formula (1)
Formula (2)
Formula (3)
Formula (4)
Formula (5)

wherein, in formulae (1) to (4), Y represents a halogen atom; $R^1$ and $R^2$ each independently represent a hydrogen atom, a sustituted or unsubstituted alkyl group having 1 to 6 carbon atoms, a substituted or unsubstituted cycloalkyl group having 3 to 6 carbon atoms, or a substituted or unsubstituted aryl group having 6 to 12 carbon atoms, or $R^1$ and $R^2$ may combine with each other to form a ring; $R^3$ represents a hydrogen atom, a substituted or unsubstituted alkyl group having 1 to 6 carbon atoms or a substituted or unsubstituted cycloalkyl group having 3 to 6 carbon atoms; and $R^4$ and $R^5$ each independently represent a substituted or unsubstituted alkyl group having 1 to 6 carbon atoms, a substituted or unsubstituted cycloalkyl group having 3 to 6 carbon atoms or a substituted or unsubstituted aryl group having 6 to 12 carbon atoms, or $R^4$ and $R^5$ may combine with each other to form a ring.

17. The process according to claim 16, wherein the quaternary ammonium salt is selected from the group consisting of tetraethylammonium bromide, tetraethylammonium iodide, benzyl tributylammonium chloride, benzyl tributylammonium iodide, benzyl triethylammonium bromide, benzyl triethylammonium chloride, benzyl trimethylammonium bromide, and benzyl trimethylammonium chloride.

18. The process according to claim 16, wherein the amount of the quaternary ammonium salt is within the range of $1.01 \times 10^{-2}$ to $5.0 \times 10^{-1}$ equivalent based on the amount of the 3-haloaniline compound represented by formula (1).

* * * * *